United States Patent [19]

Potter

[11] Patent Number: 5,571,671
[45] Date of Patent: Nov. 5, 1996

[54] METHOD FOR DETECTING ALZHEIMER'S DISEASE

[75] Inventor: Huntington Potter, Boston, Mass.

[73] Assignee: President and Fellows of Harvard College, Cambridge, Mass.

[21] Appl. No.: 216,302

[22] Filed: Mar. 23, 1994

Related U.S. Application Data

[62] Division of Ser. No. 678,683, Apr. 1, 1991, Pat. No. 5,297,562.

[51] Int. Cl.$^6$ .............................. C12Q 1/68; G01N 33/48
[52] U.S. Cl. .................................... 435/6; 435/4; 436/63; 436/811; 424/9.1; 935/76; 935/77; 935/78
[58] Field of Search ............................ 435/6, 4; 436/63, 436/811; 128/981; 935/77.78; 424/9.1

[56] References Cited

PUBLICATIONS

Podlisny et al Science (1987) 238:669–671.
Potter, H., "Review and Hypothesis: Alzheimer Disease and Down Syndrome–Chromosome 21 Nondisjunction May Underlie Both Disorders," *Am. J. Hum. Genet.*, 48:1192–1200 (1991).
Inzelberg, R., et al., "Effects of Atropine on Learning and Memory Functions in Dementia," *Clinical Neuropharmacology*, 13(3) :241–247 (1990).
Schweber, M. S., "Alzheimer's Disease and Down Syndrome," *Progress in Clinical and Biol. Research*, 317:247–267 (Alan R. Liss, Inc., 1989).
Lichter, P., et al., "Rapid Detection of Human Chromosome 21 Aberrations by in situ Hybridization," *Proc. Natl. Acad. Sci. USA*, 85:9664–9668 (1988).
Talamo, B. R., et al., "Pathological Changes in Olfactory Neurons in Patients with Alzheimer's Disease," *Nature*, 337:736–739 (1989).
Schweber, M., "A Possible Unitary Genetic Hypothesis for Alzheimer's Disease and Down Syndrome," *Anals of NY Acad. Sciences*, 450:223–238 (1985).
Madan, K., et al., "Premature Centromere Division (PCD): A Dominantly Inherited Cytogenetic Anomaly," *Hum. Genet.*, 77:193–196 (1987).
Jabs, E. W., et al., "Centromere Separation and Aneuploidy in Human Mitotic Mutants: Roberts Syndrome," *Mechanisms of Chrom. Dist. and Aneuploidy*, 111–118 (Alan R. Liss, Inc., 1989).
Uchida, I. A., et al., "Chromosome Aberrations Induced in vitro by Low Doses of Radiation: Nondisjunction in Lymphocytes of Young Adults," *Am. J. Hum. Genet.*, 27:419–429 (1975).
Romke, C., et al., "Roberts Syndrome and SC Phocomelia. A Single Genetic Entity," *Clinical Genetics*, 31:170–177 (1987).
Moorhead, P. S., and Heyman, A., "Chromosome Studies of Patients with Alzheimer Disease," *Amer. J. Of Med. Genet.*, 14:545–556 (1983).
Evans, D. A., et al., "Prevalence of Alzheimer's Disease in a Community Population of Older Persons," *JAMA*, 262(18):2551–2556 (1989).
Jarvik, L. F., et al., "Chromosomes and Mental Status," *Arch. Gen. Psychiatry.*, 30:186–190 (1974).
Matsuyama, S. S., and Jarvik, L. F., "Hypothesis: Microtubules, a Key to Alzheimer Disease," *Proc. Natl. Acad. Sci. USA*, 86:8152–8156 (1989).
Nordenson, I., et al., "Chromosomal Abnormality in Dementia of Alzheimer Type," *The Lancet*, 481–482 (March 1, 1989).
Buckton, K. E., et al., "Chromosome Changes in Alzheimer's Presenile Dementia," *J. of Med. Genet.*, 20:46–51 (1983).
Ward, B. E., et al., "Increased Aneuploidy in Alzheimer Disease," *Amer. J. Of Med. Genet.*, 3:137–144 (1979).
White, B. J., et al., "Cytogenetic Studies of Familial and Sporadic Alzheimer Disease," *Amer. J. of Med. Genet.*, 10:77–89 (1981).
Heston, L. L., and Mastri, A. R., "The Genetics of Alzheimer's Disease," *Arch. Gen. Psychiatry*, 34:976–981 (1977).
Heston, L. L., et al., "Dementia of the Alzheimer Type," *Arch. Gen. Psychiatry*, 38:1085–1090 (1981).
Lai, F., and Williams, R. S., "A Prospective Study of Alzheimer Disease in Down Syndrome," *Arch. Neurol.*, 46:849–853 (1989).
Pagon, R. A., et al., "Abnormal Skin Fibroblast Cytogenetics in Four Dysmorphic Patients with Normal Lymphocyte Chromosomes," *Am. J. Hum. Genet.*, 31:54–61 (1979).
Goate, A. M., et al., "Predisposing Locus for Alzheimer's Disease on Chromosome 21," *The Lancet*, 352–355 (Feb. 18, 1989).
Peters, G. B., et al., "Trisomy 21 Mosaicism and Maternal Age Effect," *The Lancet*, 1202–1203 (May 23, 1987).
Robison, S. H., et al., "Alzheimer's Disease Cells Exhibit Defective Repair of Alkylating Agent–Induced DNA Damage," *Anals of Neurology*, 21(3):250–258 (1987).
Hardy, J., et al., "Presenile Dementia Associated with Mosaic Trisomy 21 in a Patient with a Down Syndrome Child," *The Lancet*, 743 (Sep. 23, 1989).
Rowe, I. F., et al., "Presenile Dementia Associated with Mosaic Trisomy 21 in a Patient with a Down Syndrome Child," *The Lancet*, 229 (Jul. 22, 1989).
Harris, W. S. and Goodman, R. M., "Hyper–Reactivity to Atropine in Down's Syndrome," *N.E. J. of Med.*, 279(8):407–410 (1968).
Fitzgerald, P. H., et al., "Evidence for the Repeated Primary Non–Disjunction of Chromosome 21 as a Result of Premature Centromere Division (PCD)," *Hum. Genet.*, 72:58–62 (1986).

(List continued on next page.)

*Primary Examiner*—W. Gary Jones
*Assistant Examiner*—Carla Myers
*Attorney, Agent, or Firm*—Hamilton, Brook, Smith & Reynolds, P.C.

[57] ABSTRACT

Disclosed is a method for detecting Alzheimer's disease. The method comprises testing an individual for the presence of a mosaic population of cells in which some cells have two copies of chromosome 21 and some cells have three copies of chromosome 21. The presence of the mosaic population of cells is indicative of Alzheimer's disease in the individual.

3 Claims, No Drawings

OTHER PUBLICATIONS

Sacks, B. and Smith S., "People with Down's Syndrome can be Distinguished on the Basis of Cholinergic Dysfunction," *J. of Neurology, Neurosurgery, and Psych.*, 52:1294–1295 (1989).

Berg, J. W., et al., "Atropine in Mogolism," *Lancet*, 2:441–442 (1959).

Geller, L. N., et al., "Genetic and Clinical Links between Trisomy 21, Down Syndrome and Alzheimer's Disease," *Society for Neuroscience Abstracts*, Abstract #515.8, p. 1255 (1993).

Geller, L. N., et al., "Genetic and Clinical Links Between Trisomy 21, Down Syndrome, and Alzheimers's Disease," *The American Society for Cell Biology*, 4:246A Abstract #1426 (Dec. 1993).

Geller, L. N., et al., "Genetic and Clinical Links between Trisomy 21, Down Syndrome and Alzheimer's Disease," *Amer. J. of Human Genet.*, 53, Sep. 1993 (Supplement), Abstract #548.

METHOD FOR DETECTING ALZHEIMER'S DISEASE

RELATED APPLICATION

This application is a division of application Ser. No. 07/678,683 filed Apr. 1, 1991 now U.S. Pat. No. 5,297,562.

BACKGROUND OF THE INVENTION

It has been appreciated for some time that Alzheimer's disease has a complex etiology. At least 15 percent of the cases appear to be due to the inheritance of an autosomal-dominant mutation, but the majority are "sporadic" showing no clear association with any identifiable genetic or environmental factor. Feldman, R. G., et al., *Neurology*, 13:811–824 1963; Heston, L. L., et al., *Arch Gen. Psychiat.*, 38:1084–1090 (1981); Terry, R. D., *Aging*, 7:11–14 (1978); Jarvik, L. F. and Matsuyama, S. S., "The Biological Substrates of Alzheimer's Disease", Academic Press, pp 17–20 (1986). Even identical twins can show a large discordance in the age of onset of the disease. Nee, L. E., et al., *Neurology*, 37:359–363 (1987). Yet despite this variation, Alzheimer's disease shows a uniform set of clinical and pathological features—progressive loss of memory and other intellectual functions beginning in middle to late life, coupled with neuronal cell loss in the higher centers of the brain. Price, D. L., *Ann. Rev. Neurosci.*, 9:489–512 (1986).

When examined by histochemical stains, Alzheimer's disease brains, particularly the hippocampus, neocortex, and amygdala, exhibit certain neuropathological protein deposits that serve as the defining characteristic of the disease. One such deposit, termed the neurofibrilary tangle, occurs inside neurons and is composed of "paired helical" protein filaments (PHF). Because they can be found in other neurodegenerative diseases, paired helical filaments are likely to be a common feature of dying neurons. The more definitive lesion of Alzheimer's disease is the "neuritic or senile plaque", which consists of a spherical, extra-cellular core of filamentous protein material surrounded by a halo of degenerating nerve cell processes. Extracellular protein filaments similar to those seen in the cores of neuritic plaques also accumulate in the walls of meningeal and intracortical blood vessels. The deposits of protein filaments in the cores of neuritic plaques and in blood vessels are referred to by the generic term "amyloid".

The first identical constituent of Alzheimer amyloid deposits was purified from meningeal blood vessels and its sequence determined by Glenner, G. G. and Wong, C. W. *Biochem. Biophys. Res. Commun.*, 122:1131–1135 (1984). This protein, termed β or A4, is a ~42 amino-acid-long fragment of a larger protein that is a normal constituent of the brain and other tissues. A second protein component of Alzheimer amyloid deposits was identified as the serine protease inhibitor $\alpha_1$-antichymotrypsin (ACT).

While much has been learned about the biochemistry and expression of the aberrant protein deposits that characterize Alzheimer's disease, progress toward the development of methods for the diagnosis and treatment of the disease has been slow. This is due, at least in part, to the fact that the molecular basis for the disease pathology has remained obscure.

SUMMARY OF THE INVENTION

The subject invention relates to a method for detecting Alzheimer's disease comprising testing an individual for the presence of a mosaic population of cells. The mosaic population of cells includes normal cells having two copies of chromosome 21 and abnormal cells which contain 3 copies of chromosome 21. The mosaicism can be detected, for example, by in situ hybridization or by detecting increased sensitivity to cholinergic agonists or antagonists.

The invention enables detection of early signs of Alzheimer's disease prior to the onset of dementia. Also disclosed are methods for preventing the onset of dementia in Alzheimer's disease.

DETAILED DESCRIPTION OF THE INVENTION

Applicant's invention was made possible by the development of a mechanistic theory which provides cohesiveness to apparently disparate experimental results in Alzheimer's Disease research. A brief review of the literature is essential to an appreciation of the invention.

Perhaps the most interesting clue to the cause of Alzheimer's disease is the fact that Down syndrome patients who live beyond the age of 30 or 40 develop dementia and neuropathology essentially indistinguishable from classic Alzheimer's disease. Olson, M. I. and Shaw, C. M., *Brain*, 92:147–156 (1969); Glenner, G. G. and Wong, C. W., *Biochem. Biophys. Res. Commun.*, 122: 1131–1135 (1984); Wisniewski, H. M. and Terry, R. D., *In: Ford DH* (ed) *Progress in Brain Research*, Vol. 40, pp 1108–1109 (1988). The implication of this finding is that trisomy for chromosome 21—the pathogenetic cause of Down syndrome—is also capable of causing Alzheimer's disease, possibly through the overexpression of a gene residing on chromosome 21. Schweber, M., *Ann. NY Acad. Sci.*, 450:223–238 (1985).

On the other hand, almost all aged humans (and monkeys) develop some amyloid deposits which, by several criteria, appear to be identical to those that accumulate in much larger numbers and at an earlier time in Alzheimer's disease and Down syndrome (Wisniewski, H. M. and Terry, R. D., *In: Ford DH* (ed) *Progress in Brain Research*, Vol. 40, pp 1108–1109 (1973); Selkoe, D. J., et al., *Science*, 235:873–877 (1987); Abraham, C. R., and Potter, H., *Biotechnology*, 7:147–153 (1989). Thus, any hypothesis for the pathogenesis of Alzheimer's disease should be able to explain not only the relation between the familial and sporadic forms of the disease but also how these are related to Down syndrome and to the "normal" process of aging.

The association between Alzheimer's disease and chromosome 21 has been reinforced by a number of recent clinical and experimental findings. These, and earlier results on the genetics, epidemiology, and cell biology of Alzheimer's disease, have been considered. In particular, its association with Down syndrome has been assessed.

A molecular basis for Alzheimer's disease, which is consistent with both the genetic and sporadic forms of the disease can be explained as arising from the accumulation of chromosome 21 trisomy cells during the life of the individual. That is, trisomy 21 cells, developing over time by unequal chromosome segregation during mitosis, may ultimately lead to Alzheimer's disease through the same (as yet unknown, and perhaps multistep) mechanism by which Down syndrome patients acquire the disease, but at a later age due to the modulating effect of the mosaicism.

The first specific model linking Alzheimer's disease to Down syndrome arose when the gene for the amyloid β-protein was cloned and found to be located on chromosome 21. Goldgaber D., et al., *Science*, 235:877 (1987);

Kang, J., et al., *Nature*, 325:733 (1987); Tanzi, R. E., et al., *Science*, 235:880 (1987); Robakis, N. K., et al., *Proc. Natl. Sci. USA*, 84:4190 (1987). The implication of these results seemed that accumulation of amyloid in Alzheimer's disease was caused by the overexpression of a mutant β-protein gene or by a duplication of the β-protein gene on chromosome 21 that mimicked the gene-dosage effect of Down syndrome. The fact that some Alzheimer's disease families could be shown to harbor their autosomal dominantly-inherited mutation on chromosome 21 (St. George-Hyslop, P. H., et al., *Science*, 235:885–889 (1987)) and that the β-protein precursor gene was apparently overexpressed in Down syndrome (Tanzi R. E., et al. *Science* 235:880 (1987); Neve et al. 1988) further implicated the β-protein gene as a potential site for the disease locus.

Very recently, a variant form of the β-protein precursor gene encoding a mutant β-protein has been found in families with Hereditary Cerebral Hemorrhage with Amyloidosis of Dutch Origin, suggesting that this mutation may be the inherited defect in this disease (Van Broeckhoven C., et al. Science 248:1120–1122 (1990); Levy E. et al., Science 248:1124–1126 (1990). However, an early study suggesting that the β-protein gene existed in three copies in Alzheimer's disease patients was not confirmed. Also the pattern of expression of the β-protein gene was subtly altered in Alzheimer brain but not simply overexpressed (see Tanzi R. E. et al., Science 235:880 (1987); Neve R. L. et al., Neuron 1:669–677 (1988); Palmert M. R. et al., Science 241:1080–1084 (1988); Higgins G. A., et al., Proc. Natl. Acad. Sci. 85:1297–1301 (1988); and Golde T. E. et al., Neuron 4:253–267 (1990) for data and discussion of Alzheimer- and Down syndrome-specific changes in the expression of the several β-protein precursor mRNAs). Finally, the actual location of a potential Alzheimer's disease mutation on chromosome 21 in some families was soon shown to be far from the β-protein gene itself and closer to the centromere (Tanzi et al. 1987b; Van Broeckhoven et al. 1987; Goate et al. 1989).

The finding in some families showing no linkage to any marker on chromosome 21 suggests that the inherited form of Alzheimer's disease is genetically heterogeneous (Schellenberg et al. 1988; St. George-Hyslop et al. 1990). Chromosome 19 (Roses et a. 1990) and possibly the region of chromosome 14 now known to be close to the ACT gene (Weitkamp et al. 1983; Rabin et al. 1986) have been proposed as candidate locations for the disease locus. These results indicate that an aberrant biochemical pathway leading to the Alzheimer neuropathology can be initiated by mutation in a number of genes, including one on chromosome 21, but not the β-protein precursor gene itself.

Chromosome 21 was further implicated in the etiology of Alzheimer's disease by the discovery that some families in which Alzheimer's disease is inherited as an autosomal dominant mutation produce a significantly higher-than-normal number of Down syndrome children (Heston and Mastri 1977; Heston et al. 1981; Heyman et al. 1983). In the first study, the total number of Down's cases was 11 out of 3,044 Alzheimer's disease relatives. The mothers' ages at the birth of their children were given as 21, 26, 30, 30, 35, 39, 40, 41 and 46, plus two unknown ages. The average maternal age (34) is higher than the average maternal age for all births, which is approximately 29. However, the results would still be significant if, for instance, the children of the two or three oldest mothers were not considered (the frequency of Down syndrome is 1.3 per thousand live births to mothers of all ages). The number of relatives analyzed in the second study was 1278, including 4 Down syndrome individuals conceived to mothers of ages 26, 31, 33, and 38. These numbers are small and the average maternal age is a little high, but even if the one case of age 38 were artificially removed, the results are also statistically significant. In contrast, other researchers have failed to confirm the increased incidence of Down syndrome in families with inherited Alzheimer's disease, but they report that the number of relatives they analyzed was too few for the lack of Down syndrome to be statistically significant (Whalley et al. 1982; Amaducci et al. 1986; Chandra et al. 1987).

Recently, mouse chromosome 16, which is partially homologous to human chromosome 21, including the β-protein gene, has been shown to result, when trisomic, in neurodegeneration somewhat like that seen in Alzheimer's disease (Richards et al. 1991). Because mouse chromosome 16 is much larger and contains many more genes than does human chromosome 21, trisomy 16 mice suffer many developmental abnormalities and do not survive to term. However, the specific effect of this trisomy on the nervous system can be tested by transplanting embryonic brain tissue from a trisomy 16 embryo into the brain of a normal adult. When the brains of such host mice with their trisomy 16 grafts were examined, it was found that some of the neurons in the graft had accumulated aberrant immunoreactivity similar to that found in and around degenerating neurons in Alzheimer's disease.

Specifically, thioflavin S, a histological marker for amyloid, showed positive staining within a few cells and around some blood vessels. In addition, antisera to the β-protein precursor, to β-protein itself, to ACT, to PHF, and to phosphorylated epitopes of tau labeled a few percent of cells in the trisomy 16 grafts. There was also some extracellular staining for ACT and β-protein precursor. When dissociated cells from trisomy 16 embryos were transplanted, the effects were not observed, suggesting that cell-cell interaction or cell degeneration in the bulk trisomy 16 tissue grafts used by Richards and her colleagues may be necessary for the neuropathology to develop. Interestingly, although β-protein precursor RNA was overexpressed approximately two-fold in trisomy 16 fetal mouse brains, it was overexpressed five-fold in the brains of chimeric (mosaic) mice having 40–50% trisomy 16 cells, again suggesting that a complex cell-cell interaction affects the expression of this gene (Holtzman et al. 1990).

The most recent link between Alzheimer's disease and chromosome 21 is evidenced by reports of two women whose lymphocytes were found to be mosaic for trisomy 21 and who, though not mentally retarded, had developed Alzheimer-like dementia by age 40 (Schapiro et al. 1989; Rowe et al. 1989; for discussion, see Hardy et al. 1989). In one case the woman also had a Down syndrome child. An unusual family with an inherited aberrant chromosome 22-derived marker chromosome was found by Percy M. E., et al., Am. J. Med. Genet. (1991) to also have a high frequency of Alzheimer's disease. The two living affected members of the family carried the marker chromosome and one was also found to be mosaic for trisomy 21; only lymphocytes were analyzed from the other patient (see relevant discussion below). The two patients reported by Schapiro and Rowe and their colleagues and possibly the mosaic individual reported by Percy and her colleagues demonstrate that it is not necessary for every cell of an individual to be trisomy 21 for the aberrant effects of this chromosome imbalance to result in early Alzheimer dementia. The later onset dementia of classic Alzheimer's disease could thus result from an even smaller percentage of trisomy 21 cells that may go undetected.

Our proposal, that Alzheimer's disease and Down syndrome result from unequal chromosome 21 segregation in somatic and germ cells respectively, reconciles a seemingly diverse body of literature. For instance, one immediate implication is that any genetic or environmental factor that increases the chances of forming chromosome 21 trisomic cells should increase the likelihood of developing Alzheimer's disease. Thus, in the families in which the disease is apparently inherited as an autosomal dominant mutation near the centromere of chromosome 21, the mutation probably resides in the centromere itself so as to cause an increased frequency of nondisjunction of chromosome 21. During mitosis, such nondisjunction would build up trisomy 21 somatic cells, eventually leading to Alzheimer's disease pathology, while during meiosis it would generate trisomy 21 germ cells and Down syndrome offspring, as consistent with the epidemiological evidence. Indeed, there are centromere mutations known in yeast that result in a 100-fold increase in chromosome nondisjunction (Gaudet and Fitzgerald-Hayes 1987).

Of course chromosome segregation is a complex process under the control of many gene products (for review, see Murray and Szostak 1985), and an inherited disorder of chromosome segregation could be caused by mutations at a number of loci. In this light, the fact that familial Alzheimer's disease appears to be genetically heterogeneous is not surprising, since any one of several mutations could lead to the development of trisomy 21 cells, both somatic and germline, with the consequent development of Alzheimer's disease in the individual and an increased frequency of Down syndrome offspring. Several researchers have suggested that a specific microtubule defect could lead directly to the neuronal pathology and indirectly to the increase in Down's offspring in Alzheimer's disease through chromosome nondisjunction (Heston and Mastri 1977; Nordenson et al. 1980; Matsuyama and Jarvik 1989).

Although improper chromosome segregation can result from a genetic mutation, it can also be caused by environmental agents. Of the many exogenous factors that influence chromosome segregation, microtubule-disrupting agents such as colchicine and low doses of radiation are perhaps the best studied (see, for example, Uchida et al. 1975). Aluminum, the consumption of which shows a weak, but significant association with the development of Alzheimer's disease (see, for example, Martyn et al. 1989), also binds to microtubules and, in the form of aluminum silicate, causes chromosome nondisjunction in cultured cells (Paleker et al. 1987; for discussion see Ganrot 1986). Thus, the large proportion of Alzheimer's disease cases that arise in a sporadic manner not directly attributable to the inheritance of a genetic mutation can also be understood in the light of the chromosome 21 trisomy model.

An important prediction of this model is that it is the dividing cells in an individual that are most likely to develop chromosome 21 trisomy and lead to Alzheimer's disease. Extensive analysis by Rakic (1985) has shown that the only dividing cells in the brains of adult monkeys exposed to $^3$H-thymidine are glial cells and the endothelial cells lining blood vessels, while neurons, the cells most apparently affected by Alzheimer's disease, do not divide. The labeled glia were seen primarily in the hippocampus and the cerebral cortex. Thus cell division in the brains of adult primates occurs in those general regions that develop neuropathology in Alzheimer's disease, Down syndrome, and normal aging. Interestingly, astroglia in the hippocampus and cortex of Alzheimer's disease brain overexpress ACT, and astrocytes can be induced by kainic acid lesions to overexpress the β-protein precursor (Pasternack et al. 1989; Siman et al. 1989; for discussion of how overexpression of ACT or β-protein precursor can lead to amyloid formation, see Abraham and Potter 1989).

Recently, two rapidly dividing peripheral tissues (skin and intestinal mucosa) have been reported to contain pre-amyloid deposits of β-protein in sporadic Alzheimer patients and some aged, normal subjects (Joachim et al. 1989). Another region of active cell division, which has been shown to exhibit pathological changes in Alzheimer's disease, is the olfactory epithelium (Talamo et al. 1989). Thus there seems to be a rough correlation between regions of cell division and areas where Alzheimer pathology can develop. Of course, mitotic nondisjunction could also occur early enough in embryogenesis to generate trisomy 21 in nondividing adult cells such as neurons.

Although it would seem reasonable that amyloid should develop in the regions immediately surrounding aberrant cells (for instance trisomy 21 cells), the precedent provided by other amyloidoses suggests that this need not be the case. For instance, the autosomal-dominantly inherited diseases Familial Amyloidotic Polyneuropathy and Hereditary Cerebral Hemorrhage with Amyloidosis of both the Dutch and Icelandic types have very specific regions of amyloid deposition despite the fact that all cells in the body carry the point mutation in the affected amyloid gene (transthyretin, cystatin C, or β-protein precursor, respectively), and that these genes are expressed in many parts of the body where the amyloid does not deposit (for review see Castano and Frangione 1988). Thus, by analogy, the trisomy 21 cells that are relevant for the formation of amyloid pathology in Down syndrome (and, according to the hypothesis, Alzheimer's disease) need not reside in the brain at all. Indeed, some researchers believe that the β-protein is transported to the brain by the circulation, having been generated elsewhere (see, for example, Selkoe 1989b for recent data and discussion).

In sum, both genetic and sporadic forms of Alzheimer's disease can be explained as arising from the effects of trisomy 21 cells accumulating during the life of the individual. A propensity to develop such cells can be genetic in origin (either due to an aberrant chromosome 21 centromere or to a mutation elsewhere in the genome affecting all chromosome segregation), or it can be caused by environmental factors. A combination of genetic and environmental influences on the formation of trisomic 21 cells is responsible for the observed variation in the age of onset of Alzheimer's disease in identical twins and in Alzheimer's disease families. In addition, the fact that almost 50% of the population over the age of 85 show some symptoms of Alzheimer's disease dementia (Evans et al. 1989), and an even larger proportion show some of the same neuropathological lesions, indicates that all individuals may, to some degree, be subject to stochastic events that lead to aberrant chromosome segregation with increasing age. The possibility that further biochemical or genetic events may be required before full Alzheimer neuropathology arises is indicated by the mature age (20's to 30's) that Down syndrome patients begin to accumulate amyloid deposits.

Cytogenetic analysis of Alzheimer's disease patients has been carried out in a number of laboratories, with mixed reports of increased aneuploidy or other abnormalities as measured directly (Jarvik et al. 1974; Ward et al. 1979; Nordenson et al. 1980; White et al. 1981; Buckton et al. 1983; Moorhead and Heyman 1983). Furthermore, premature centromere division (PCD), a correlate and potential cause of improper chromosome segregation in vitro and in vivo, was found to be positively correlated with age and to be increased in women with familial Alzheimer's disease (3.6% vs. 0.6% in age-matched controls), particularly affecting the X chromosome (Fitzgerald et al. 1975; Moorhead and Heyman 1983). Trisomy 21, 18 and X occurred in the lymphocytes and fibroblasts of a woman apparently prone to PCD, who also had three trisomy conceptuses (Fitzgerald et al. 1986). Patients with Roberts syndrome, a rare autosomal recessive disorder characterized by growth and mental retardation and craniofacial abnormalities, also shows PCD—there can be significant aneuploidy, usually involving chromosome loss rather than gain (except for trisomy 7) (see Romke et al. 1987; Jabs et al. 1987). PCD can also be found that appears limited to the X chromosome and results, presumably by nondisjunction, in many cells with one or three X chromosomes (Fitzgerald et al. 1975). Other Roberts syndrome families with extensive PCD have been found that exhibit normal karyotypes and phenotypes (Madan et al. 1987). Thus PCD need not result in nondisjunction, but when it does, severe developmental abnormalities can result if the autosomes are affected. The report by Fitzgerald and his colleagues (1986) is the only case of PCD in which trisomy of chromosomes other than the X chromosome were prevalent. Why Roberts syndrome generally results in chromosome loss rather than gain is not clear. Perhaps because of the severe mental retardation exhibited by these patients, neurological and pathological tests for Alzheimer's disease have not been reported.

The fact that the chromosomes that exhibit PCD in an individual do not necessarily correspond to those which ultimately are lost or gained to give an aberrant karyotype (there is a prevalence of trisomy 21, 18 and X in the general PCD case of Fitzgerald et al. (1986), probably reflects differential cell viability. For instance, lymphocyte cultures from trisomy 21 mosaic individuals often show a lower proportion of trisomy cells than do, for instance, fibroblast cultures, and some patients with over 10% trisomy fibroblasts can show a normal karyotype in lymphocytes (out of, for example, 30 metaphases) (Pagon et al. 1979; Ford 1981).

Thus, the fact that cytogenetic studies on Alzheimer patients have almost always relied on peripheral blood lymphocytes (for example Jarvik et al. 1974; Ward et al. 1979; Nordenson et al. 1980; White et al. 1981; Buckton et al. 1983; Moorhead and Heyman 1983) may have prevented trisomy 21 mosaicism from being detected and linked to Alzheimer's disease. In these studies, fewer than 100 or even 50 lymphocyte metaphases per sample were examined, and the few percent with increased aneuploidy (generally a loss) for any chromosome in Alzheimer's disease was usually not significantly different from controls. The specific frequency of trisomy 21 was too low to be useful or was not stated.

The mechanism proposed herein can be tested by analysis of dividing cells from affected areas of the brain—glia, endothelial cells of the meningeal and cortical vessels, and the olfactory epithelium—and possibly of skin fibroblasts. Procedures have recently been developed (Lichter et al. 1988; Fuscoe et al. 1989) that allow the number of chromosome 21s to be counted in both metaphase and interphase nuclei. The methodology is based on in situ hybridization with, for instance, biotin-labeled chromosome 21-specific probes that are then visualized by fluoresceine-labeled streptavidin. The advantage of this approach over standard cytogenetics is that both dividing and non-dividing cells can be studied, and, more important, the number of chromosomes in interphase nuclei in tissue sections can be counted (Lichter et al. 1988). Because the number of cells that might harbor three copies of chromosome 21 in Alzheimer's brain or peripheral tissue might be very small, the finding of a small cluster of trisomy cells would be far more significant than the same number of cells found one at a time among a population of thousands of other cells after they have been disaggregated and induced to divide in culture to yield metaphase chromosome spreads. The large number of "normal" aged individuals that show some symptoms of Alzheimer's disease and some Alzheimer pathology (neurofibrillary tangles and amyloid deposits) will make it necessary to carry out careful comparisons between Alzheimer's disease patients and age-matched controls. Such an analysis would, of course, be made easier by concentrating on earlier onset (often familial) Alzheimer's cases. Although initial studies would seem to be best directed at searching for trisomy 21 cells in the brain, the possibility (discussed above) that Alzheimer amyloid deposits may arise from aberrant cells in the periphery suggests that a similar in situ hybridiztion analysis should also be carried out on various other tissues, for instance skin and the intestinal mucosa.

If Alzheimer's disease patients are found to be mosaic for trisomy 21, then we might expect them to exhibit some other abnormalities of Down syndrome in addition to dementia—for example, hypersensitivity to acetylcholine agonists and antagonists (Berg et al., 1959; Harris and Goodman, 1968; Sacks and Smith, 1989). Such characteristics, together with in situ hybridization for chromosome 21, form the basis of a diagnostic test for Alzheimer's disease.

Diagnosis for Alzheimer's disease before symptoms of dementia arise can be accomplished by determining whether the individual is indeed mosaic for trisomy 21. This can be carried out either directly by in situ hybridization as described above, or indirectly by measuring certain characteristics known to be associated with Down syndrome that arise due to the trisomy 21 nature of this disorder, and assay them for their presence in a suspected Alzheimer patient. Examples of such Down's patient features include Brushfield spots on the irises (Grouchy and Turleau, 1984), hypersensitivity of heart rate, pupil contraction, and sweat production to acetylcholine agonists and antagonists (Berg et al., 1959); Harris and Goodman, 1968; Symon et al. 1985; Reyes et al., 1987; Sacks and Smith, 1989, Inzelberg et al., 1990). Many methods for monitoring hypersensitivity to cholinergic agonists and antagonists are well known in the art. In short, any characteristic of Down syndrome may be used as a basis for designing a diagnostic test for Alzheimer's disease.

Because the data indicate that Alzheimer's disease is a mosaic form of Down syndrome due to nondisjunction (but perhaps during meiosis followed by nondisjunction early in development to yield normal cells), much Alzheimer's disease may be prevented by preventing the nondisjunction from occurring, including such approaches as avoiding environmental agents that cause translocation by inducing chromosome nondisjunction, treatment with agents that reduce spontaneous nondisjunction or that obviate the effects of environmental agents, and mitotic inhibitors such as colcemid or methyl benzimidazole-2-yl-carbamate. Such treatment might include, but is not limited to, heavy metal chelaters, antioxidants, and promoters of microtubule assembly. Drugs that improve chromosome segregation will include those that affect DNA toposiomerase II(Holm et al., 1989), or centromere binding proteins such as CBF1 (Cai and Davis, 1990), or DYS1 (Rockmill and Fogel, 1988). An additional approach may be to treat patients with drugs to which trisomy 21 cells may be particularly sensitive in the expectation that they will be preferentially killed and thus no longer pose a threat to the patient. This may be accomplished by killing cells that have an excess of certain cell surface markers known to be increased in cells from Down syndrome patients due to the trisomy 21. These include the cell surface marker S14 and interferon-α receptor (Grouchy and Turlow, 1984).

References

Abraham C. R., Selkoe D. J., Potter H. (1988) Immunochemical identification of the serine protease inhibitor $\alpha_1$-antichymotrypsin in the brain amyloid deposits of Alzheimer's disease. Cell 52:487–501

Abraham C. R., Potter H. (1989) Alzheimer's disease: Recent advances in understanding the brain amyloid deposits. Biotechnology 7:147–153

Abraham C. R., Selkoe D. J., Potter H., Price D. C., Cork L. C. (1989) $\alpha_1$-antichymotrypsin is present together with the β-protein in monkey brain amyloid deposits. Neumscience 32:715–720

Amaducci L. A., Fratiglioni L., Rocca W. A., Reschi C., Uvrea P., Pedone D., Bracco L. et al (1986) Risk factors for clinically diagnosed Alzheimer's disease: a case-control study of an Italian population, Neurology 36:922–931

Ault B., Fine A., Rappaport S. I. (1990) Mouse trisomy 16 neurons maintained by neural transplantation: a possible model of neuropathology in Alzheimer's disease. Soc Neurosci Abs 555.10

Buckton K. E., Whalley L. J., Lee M., Christie J. E. (1983) Chromosome changes in Alzheimer's presenile dementia. J Med Genet 20:46–51

Castano E. M., Frangione B. (1988) Biology of disease: Human amyloidosis, Alzheimer disease and related disorders. Lab Invest 58:122–132.

Chandra V., Philipose V., Bell P. A., Lazaroff A., Schoenberg B. S. (1987) Case-control study of late onset "probable Alzheimer's disease." Neurology 37:1295–1300

Evans D. A., Funkenstein H., Albert M. S., Scherr P. A., Cook N. R., Chown M. J., Hebert L. E., et al (1989) Prevalence of Alzheimer's disease in a community population of older persons. JAMA 262:2551–2556

Feldman R. G., Chandler K. A., Levy L., Glaser G. H. (1963) Familial Alzheimer's disease. Neurology 13:811–824

Fitzgerald P. H., Pickering A. F., Mercer J. M., Miethke P. M. (1975) Premature centromere division: a mechanism of non-disjunction causing X chromosome aneuploidy in somatic cells of man. Ann Hum Genet 38:417–428

Fitzgerald P. H., Archer S. A., Mords C. M. (1986) Evidence for the repeated primary non-disjunction of chromosome 21 as a result of premature centromero division (PCD). Hum Genet 72:58–62

Ford C. E. (1981) Nondisjunction. In: Burgio G. R., Fraccaro M., Tiepolo L., Wold U (eds) Trisomy 21, Springer, Berlin, Heidelberg, New York, pp 103–143

Fuscoe J. C., Collins C. C., Pinkel D., Gray J. W. (1989) An efficient method for selecting unique-sequence clones from DNA libraries and its application to fluorescent staining of human chromosome 21 using in situ hybridization. Genomics 5:100–109

Ganrot P. O. (1986) Metabolism and possible health effects of aluminum. Environ Health Persp 65:363–441

Gaudet A., Fitzgerald-Hayes M. (1987) Alterations in the adenine-plus-thymine-rich region of CEN3 affect centromere function in Saccharomyces cerevisiae. Mol Cell Biol 7:68–75

Glenner G. G., Wong C. W. (1984a) Alzheimer's disease: initial report of the purification and characterization of a novel cerebrovascular amyloid protein. Biochem Biophys Res Commun 122:885–890

Glenner G. G., Wong C. W. (1984b) Alzheimer's disease and Down's syndrome: Sharing of a unique cerebrovascular amyloid fibril protein. Biochem Biophys Res Commun 122:1131–1135

Goate A. M., Owen M. J., James L. A., Mullan M. J., Rossor M. N., Haynes A. R., Farral M., et al (1989) Predisposing locus for Alzheimer's disease on chromosome 21. Lancet, February 18:352, 1989

Goide T. E., Estus S., Usiak M., Younkin L. H., Younkin S. G. (1990) Expression of β amyloid protein precursor mRNAs: Recognition of a novel alternatively spliced form and quantitation in Alzheimer's disease using PCR. Neuron 4:253–267

Goldgaber D., Lerman M. J., McBride O. W., Saffiotti V., Gadjusek D. C. (1987) Characterization and chromosomal localization of a cDNA encoding brain amyloid of Alzheimer's disease. Science 235:877

Hardy J., Goate A., Owen M., Rossor M. (1989) Presenile dementia associated with mosaic trisomy 21 in a patient with a Down syndrome child. Lancet, September 23:743

Heston L. L., Mastd A. R. (1977) The genetics of Alzheimer's disease: Associations with hematologic malignancy and Down's syndrome. Arch Gen Psychiatry 34:976–981

Heston L. L., Mastd A. R., Anderson V. E., White J. (1981) Dementia of the Alzheimer type. Clinical genetics, natural history, and associated conditions. Arch Gen Psychiat 38:1084–1090

Heyman A., Wilkinson W., Hurwitz B., Schmechel D., Sigmon A., Weinberg T., Helms M., Swift M. (1983) Alzheimer's disease: Genetic aspects and associated clinical disorders. Ann Neurol 14:507–515

Higgins G. A., Lewis D. A., Bahmanyar S., Goldgaber D., Gajdusek D. C., Young W. G., Mordson J. H., Wilson M. C. (1988) Differential regulation of amyloid-β-protein mRNA expression within hippocampal neuronal subpopulations in Alzheimer disease. Proc Natl Acad Sci 85:1297–1301

Holtzman D. M., Bayney R. M., Berger C. N., Epstein C. J., Mobley W. C. (1990) Altered developmental and tissue specific regulation of gene expression in mouse trisomy 16. Soc Neurosci Abs. 469.6

Jabs E. W., Tuck-Muller C. M., Cusano R., Rattner J. B. (1989) Centromere separation and aneuploidy in human mitotic mutants: Roberts syndrome. Prog Clin Biol Res 318:111–118

Jarvik L. F., Yen F.-S., and Goldstein F. (1974) Chromosomes and mental status. A study of women residing in institutions for the elderly. Arch Gen Psychiat 30:186–190

Jarvik L. F., Matsuyama S. S. (1986) Dementia of the Alzheimer type. In: Scheibel A. B., Wechslev A. F. (eds)The Biological Substrates of Alzheimer's Disease. Academic Press, Orlando, Fla., pp 17–20

Joachim C. L., Mori H., Selkoe D. J. (1989) Amyloid β-protein deposition in tissues other than brain in AD. Nature 341:226–230

Kang J., Lemaire H. G., Unterback A., Salbaum J. M., Masters C. L., Grezeschik K. H., Multhaup G., Beyreuther K., Müller-Hill B. (1987) The precursor of Alzheimer disease amyloid A4 protein resembles a cell-surface receptor. Nature 325:733

Levy E., Carman M. D., Fernandez-Madrid I. J., Lieberburg I., Power M. D., van Duinen S. G., Bots GThAM, Luyendijk W., Frangione B. (1990) Mutation of the Alzheimer's disease amyloid gene in Hereditary Cerebral Hemorrhage, Dutch type. Science 248:1124–1126

Lichter P., Cremer T., Tang C.-J. C., Watkins P. C., Manuelidis L., Ward D. C. (1988) Rapid detection of human chromosome 21 aberrations by in situ hybridization. Proc Natl Acad Sci USA 85:9664–9668

Madan K., Lindhout D., Palan A. (1987) Premature centromere division (PCD): a dominantly inherited cytogenetic anomaly. Hum Genet 77:193–196

Martyn C. N., Osmond C., Edwardson J. A., Barker D. J. P., Harris E. C., Lacey R. F. (1989) Geographical relation between Alzheimer's disease and aluminum in drinking water. Lancet 14 January:59–62

Matsuyama S. S., Jarvik L. F.: Hypothesis (1989) Microtubules, a key to Alzheimer's disease. Proc Natl Acad Sci 86:8152–8156

Moorhead P. S., Heyman A. (1983) Chromosome studies of patients with Alzheimer disease. Am J Med Genet 14:545–556

Murray A. W., Szostak J. W. (1985) Chromosome segregation in mitosis and meiosis. Annu Rev Cell Biol 1:289–315

Müller-Hill B., Beyreuther K. (1989) Molecular biology of Alzheimer's disease. Annu Rev Biochem 58:287–307

Nee L. E., Eldridge R., Sunderland T., Thomas C. B., Katz D., Thompson K. E., Weingartner H., et al (1987) Dementia of the Alzheimer type: Clinical and family study of 22 twin pairs. Neurology 37:359–363

Neve R. L., Finch E. A., Dawes L. R. (1988) Expression of the Alzheimer amyloid precursor gene transcripts in the human brain. Neuron 1:669–677

Neve R. L., Potter H. (1991) Molecular biology of Alzheimer amyloid plaque proteins. In: Brosius J., Fremeau R. (eds) Molecular Genetic Approaches to Neuropsychiatric Disease, Academic Press, Orlando, Fla. (in press)

Nordenson I., Adolfsson R., Beckman G., Bucht G., Winblad B. (1980) Chromosomal abnormality in dementia of Alzheimer type. Lancet Mar. 1, 1980, 481–482

Olson M. I., Shaw C. M. (1969) Presenile dementia and Alzheimer's disease in mongolism. Brain 92:147–156

Pagon R. A., Hall J. G., Davenport S. L. H., Aase J., Norwood T. H., Hoehn H. W. (1979) Abnormal skin fibroblast cytogenetics in four dysmorphic patients with normal lymphocyte chromosomes. Am J Hum Genet 31:54–61

Palekar L. D., Eyre J. F., Most B. M., Coffin D. L. (1987) Metaphase and anaphase analysis of V79 cells exposed to edonite, UICC chrysotile, and UICC crocidolite. Carcinogen 8:553–560

Palmert M. R., Golde T. E., Cohen M. L., Kovacs D. M., Tanzi R. E., Gusella J. F., Usiak M. F., Younkin L. H., Younkin S. G. (1988) Amyloid protein precursor messenger RNAs: Differential expression in Alzheimer's disease. Science 241:1080–1084

Pasternack J. M., Abraham C. R., Van Dyke B., Potter H., Younkin S. G. (1989) Astrocytes in Alzheimer's disease gray matter express $\alpha_1$-antichymotrypsin mRNA. Am J Pathol 135:827–834

Percy M. E., Markovic V. D., McLachlan D. R. C., Berg J. M., Hummel J. T., Laing M. E., Dearie T. G., Andrews D. F. (1991) A family with a 22-derived marker chromosome and late-onset dementia of the Alzheimer type: I. Application of a new model for estimation of the risk of disease associated with the marker. Am J Med Genet (in press)

Price D. L. (1986) New perspectives in Alzheimer's disease. Ann Rev Neurosci 9:489–512

Rabin M., Watson M., Kidd V., Woo S. L. C., Breg W. R., Ruddle F. H. (1986) Regional location of $\alpha_1$-antichymotrypsin and $\alpha_1$-antitrypsin genes on human chromosome 14. Somatic Cell Mol Genet 12:209–214

Rakic P. (1985) Limits of neurogenesis in primates. Science 227:1054–1056

Richards S.-J., Waters J. J., Wischik C. M., Abraham C. R., Sparkman D. R., White C. L., Beyreuther K., et al (1991) Transplants of mouse trisomy 16 hippocampus provide an in vivo model of the neuropathology of Alzheimer's disease. EMBO J (in press)

Robakis N. K., Ramakrishna N., Wolfe G., Wisniewski H. M. (1987) Molecular cloning and characterization of a cDNA encoding the cerebrovascular and the neuritic plaque amyloid peptides. Proc Natl Acad Sci USA 84:4190

Roses A. D., Pericak-Vance M. A., Clark C. M., Gibert J.-R., Yamaoka L. H., Haynes C. S., Speer M. C., et al (1990) Linkage studies of late-onset familial Alzheimer's disease. Adv Neurol 51:185–196

Römke C., Froster-Iskenius U., Heyne K., Höhn W., Hof M., Grzejszczyk G., Rauskolb R., et al (1987) Roberts syndrome and SC phocomelia. A single genetic entity. Clin Genet 31:170–177

Rowe I. F., Ridler M. A. C., Gibberd F. B. (1989) Presenile dementia associated with mosaic trisomy 21 in a patient with a Down syndrome child. Lancet, July 22, 229

Schapiro M. B., Kumar A., White B., Grady C. L., Friedland R. P., Rapoport S. I. (1989) Alzheimer's disease (AD)in mosaic/translocation Down's syndrome (Ds) without mental retardation. Neurology 39 (Suppl. 1):169

Schellenberg G. D., Bird T. D., Wijsman E. M., Moore D. K., Boehnke M., Bryant E. M., Lampe T. H., et al (1988) Absence of linkage of chromosome 21q21 markers to familial Alzheimer's disease. Science 241:1507–1510

Schweber M. (1985) A possible unitary genetic hypothesis for Alzheimer's disease and Down syndrome. Ann NY Acad Sci 450:223–238

Selkoe D. J. (1989a) Biochemistry of altered brain proteins in Alzheimer's disease. Annu Rev Neurosci 12:493–520

Selkoe D. J. (1989b) Molecular pathology of amyloidogenic proteins and the role of vascular amyloidosis in Alzheimer's disease. Neurobiol Aging 10:387–3395

Selkoe D. J., Bell D. S., Podlisny M. B., Price D. L., Cork L. C. 1987) Conservation of brain amyloid proteins in aged mammals and humans with Alzheimer's disease. Science 235:873–877

Siman R., Card J. P., Nelson R. B., Davis L. G. (1989) Expression of β-amyloid precursor protein in reactive astrocytes following neuronal damage. Neuron 3:275–285

St. George-Hyslop P. H., Tanzi R. E., Polinsky R. J., Haines J. L., Nee L., Watkins P. C., Myers R. H., et al (1987) The genetic defect causing familial Alzheimer's disease maps on chromosome 21. Science 235:885–889

St. George-Hyslop P. H., Haines J. L., Farrer L. A., Polinsky R., Van Broeckhoven C., Goate A., McLachlan D. R. O., et al (1990) Genetic linkage studies that Alzheimer's disease is not a single homogeneous disorder. Nature 347:194–197

Talamo B. R., Rudel R. A., Kosik K. S., Lee V. M.-Y., Neff S., Adelman L., Kauer J. S. (1983) Pathological changes in olfactory neurons in patients with Alzheimer's disease. Nature 337:736–739

Tanzi R. E., Gusella J. F., Watkins P. C., Bruns G. A. P., St. George-Hyslop P., Van Keuren M. L., Patterson D., et al (1987a) Amyloid β-protein gene; cDNA, mRNA distributions, and genetic linkage near the Alzheimer locus. Science 235:880

Tanzi R. E., St George-Hyslop P. H., Haines J. L., Polinsky R. J., Nee L., Foncin J.-F., Neve R. L., et al (1987b) The genetic defect in familial Alzheimer's disease is not tightly linked to the amyloid β-protein gene. Nature 329:156–157

Terry R. D. (1978) Aging, senile dementia, and Alzheimer's disease. Aging 7:11–14

Uchida I. A., Lee C. P. V., Byrnes E. M. (1975) Chromosome aberrations in vitro by low doses of radiation: Nondisjunction in lymphocytes of young adults. Am J Hum Genet 27:419–429

Van Broeckhoven C., Genthe A. M., Vandenberghe A., Horsthemke B., Backhovens H., Raeymaekers P., Van Hul W., et al (1987) Failure of familial Alzheimer's disease to segregate with the A4-amyloid gene in several European families. Nature 329:153–155

Van Broeckhoven C., Hann J., Bakker E., Hardy J. A., Van Hul W., Wehnert A., Vegter-Van der Vlis M., et al (1990) Amyloid β protein precursor gene and Hereditary Cerebral Hemorrhage with Amyloidosis (Dutch). Science 248:1120–1122

Ward B. E., Cook R. H., Robinson A., Austin J. H. (1979) Increased aneuploidy in Alzheimer disease. Am J Med Genet 3:137–144

Weitkamp L. R., Nee L., Keats B., Polinsky R. J., Guttormsen S. (1983) Alzheimer disease: evidence for susceptibility loci on chromosomes 6 and 14. Amer J Hum Genet 35:443–453

Whalley L. J., Carothers A. D., Collyer S., De May R., Frackiewicz A. (1982) A study of familial factors in Alzheimer's disease. Brit J Psychiat 140:249–256

White B. J., Crandall C., Goudsmit J., Morrow C. H., Alling D. W., Gajdusek D. C., Tjio J. H. (1981) Cytogenetic studies of familial and sporadic Alzheimer disease. Am J Med Genet 10:77–89

Wisniewski H. M., Terry R. D. (1973) Morphology of the aging brain, human and animal. In: Ford DH (ed) Progress in Brain Research, Vol. 40, Neurobiological Aspects of Maturation and Aging, Elsevier, Amsterdam, pp 1108–1109

Wisniewski H. M., Rabe A., Wisniewski K. E. (1988) Neuropathology and dementia in people with Down's syndrome. In: Davies P., Finch C., (eds) Molecular Neuropathology of Aging, Banbury Report, Cold Spring Harbor Laboratory, New York, pp 399–413

Equivalents

Those skilled in the art will know, or be able to ascertain using no more than routine experimentation, many equivalents to the specific embodiments of the invention described herein. These and all other equivalents are intended to be encompassed by the following claims.

I claim:

1. A method for screening for an increased likelihood of alzheimer's disease in an individual comprising testing the individual for the presence of a mosaic population of cells containing two copies of chromosome 21 and cells containing three copies of chromosome 21, wherein the presence of the mosaic population of cells is indicative of an increased likelihood of Alzheimer's disease in the individual.

2. A method of claim 1 wherein the cells which have three copies of chromosome 21 are distinguished from the cells having two copies of chromosome 21 by in situ hybridization using a nucleic acid probe which hybridizes specifically to chromosome 21.

3. A method of claim 2 wherein the in situ hybridization is conducted on olfactory epithelium or skin cell biopsy samples.

* * * * *

UNITED STATES PATENT AND TRADEMARK OFFICE
CERTIFICATE OF CORRECTION

PATENT NO. : 5,571,671
DATED : November 5, 1996
INVENTOR(S) : Huntington Potter

It is certified that error appears in the above-identified patent and that said Letters Patent is hereby corrected as shown below:

Column 1, line 7, insert the following information:

---GOVERNMENT FUNDING

This invention was made with Government support under NIH Grants AG08084 and GM35967 awarded by the National Institutes of Health. The Government has certain rights in the invention.---

Signed and Sealed this

Twenty-eighth Day of October, 1997

Attest:

BRUCE LEHMAN

Attesting Officer

Commissioner of Patents and Trademarks